US009790227B2

United States Patent
Chupakhin et al.

(10) Patent No.: US 9,790,227 B2
(45) Date of Patent: Oct. 17, 2017

(54) 2-METHYLSULPHANYL-6-NITRO-7-OXO-1, 2, 4-TRIAZOLO [5, 1-C] [1, 2, 4] TRIAZINIDE L-ARGININE DIHYDRATE ACTIVE TOWARD WEST NILE VIRUS

(71) Applicant: LIMITED LIABILITY COMPANY "URAL CENTER OF BIOPHARMACEUTICAL TECHNOLOGY", Novouralsk, Sverdlovskaya obl. (RU)

(72) Inventors: Oleg Nikolaevich Chupakhin, Yekaterinburg (RU); Vladimir Leonidovich Rusinov, Yekaterinburg (RU); Evgeny Narcissovich Ulomsky, Yekaterinburg (RU); Konstantin Valerievich Savateev, Yekaterinburg (RU); Stepan Sergeevich Borisov, Sverdlovskaya obl. (RU); Natalia Alexandrovna Novikova, Yekaterinburg (RU); Svetlana Yakovlevna Loginova, Moskovskaya obl. (RU); Sergey Vladimirovich Borisevich, Moskovskaya obl. (RU); Pavel Vladimirovich Sorokin, Yekaterinburg (RU)

(73) Assignee: LIMITED LIABILITY COMPANY "URAL CENTER OF BIOPHARMACEUTICAL TECHNOLOGY", Novouralsk, Sverdlovskaya obl. (RU)

( * ) Notice: Subject to any disclaimer, the term of this patent is extended or adjusted under 35 U.S.C. 154(b) by 0 days.

(21) Appl. No.: 15/033,433

(22) PCT Filed: Oct. 21, 2014

(86) PCT No.: PCT/RU2014/000794
§ 371 (c)(1),
(2) Date: Jul. 13, 2016

(87) PCT Pub. No.: WO2015/065243
PCT Pub. Date: May 7, 2015

(65) Prior Publication Data
US 2016/0318934 A1    Nov. 3, 2016

(30) Foreign Application Priority Data

Nov. 1, 2013    (RU) .............................. 2013148984

(51) Int. Cl.
C07D 487/04    (2006.01)
A61K 31/53     (2006.01)
C07C 279/14    (2006.01)

(52) U.S. Cl.
CPC ............ *C07D 487/04* (2013.01); *A61K 31/53* (2013.01); *C07C 279/14* (2013.01)

(58) Field of Classification Search
CPC combination set(s) only.
See application file for complete search history.

(56) References Cited

U.S. PATENT DOCUMENTS 4,005,133 A * 1/1977 Morozowich ......... C07C 405/00
562/503

FOREIGN PATENT DOCUMENTS

| IN | EP 1918289 A2 * | 5/2008 | ........... C07D 455/04 |
|---|---|---|---|
| RU | 2058307 C1 | 4/1996 | |

(Continued)

OTHER PUBLICATIONS

Odelola, "Antiviral activity of Virazole on replication of viruses isoleted in Nigeria", Siegenthaler W., Lathy R. editors, Current chemotherapy, Washington: American Society of Microbiology, 1978, vol. 1, pp. 334-335.
Jordan et al., "Ribavirin inhibits West Nile virus replication and cytopathic effect in neural cells", The Journal of Infectious Diseases, 2000, vol. 182, pp. 1214-1217.
Shahar et al., "Different pathogenicity of encephalitic togaviruses in organotypic cultures of spinal cord slices", Journal of Neuroscience Research,1990, vol. 25., pp. 345-352.
Anderson et al., "Efficacy of interferon alpha-2b and ribavirin against West Nile virus in vitro", Emerging Infectious Diseases, 2002, vol. 8, No. 1, pp. 107-108.
Loginova et al., "Antiviral activity of interferon inducers of Amiksin in experimental form of West Nile fever", Questions of Virology, 2004, No. 2, pp. 8-11, http://www.fesmu.ru/elib/Article.aspx?id=108328.

(Continued)

*Primary Examiner* — Michael Barker
*Assistant Examiner* — Amanda L Aguirre
(74) *Attorney, Agent, or Firm* — BCF LLP

(57) ABSTRACT

The claimed invention relates to the field of biologically active compounds and concerns 2-methylsulphanyl-6-nitro-7-oxo-1,2,4-triazolo[5,1-c][1,2,4]triazinide L-arginine dihydrate, which exhibits an antiviral effect and is intended for the treatment and prophylaxis of human and animal viral diseases, primarily West Nile Virus, and can be used in the chemical and pharmaceutical industry, in scientific research laboratories and medical facilities, and also in veterinary science. The claimed invention is directed toward achieving the technical result of creating a novel effective drug of the azoloazine variety which exhibits antiviral activity toward a group of RNA-containing viruses, and reducing the dependence of the active compound on cell metabolism. This technical result is achieved in the creation of the novel drug 2-methylsulphanyl-6-nitro-7-oxo-1,2,4-triazolo[5,1-c][1,2,4]triazinide L-arginine dihydrate, which exhibits an aniviral effect and has the formula (I). This technical result is achieved in that a method for producing 2-methylsylphanyl-6-nitro-7-oxo-1,2,4-triazolo[5,1-c][1,2,4]triazinide L-arginine dihydrate includes mixing arginine, dissolved in water, and 2-methylthio-6-nitro-7-oxo-1,2,4-triazolo[5,1-c][1,2,4] triazinide sodium dihydrate, dissolved in a (1:1) water-ethanol mixture, whereupon the resultant mixture is boiled then cooled, and the precipitate is filtered off and dried.

3 Claims, No Drawings

(56) References Cited

FOREIGN PATENT DOCUMENTS

| RU | 2294936 C1 | 3/2007 |
|---|---|---|
| RU | 2365591 C2 | 8/2009 |
| RU | 2402552 C2 | 10/2010 |
| WO | 2007039146 A1 | 4/2007 |

OTHER PUBLICATIONS

Loginova et al., "Ribavirin Prophylaxis and Therapy of Experimental West Nile Fever", Antibiotics and Chemotherapy, 2009, vol. 54, Nos. 11-12, pp. 17-20.

Loginova et al., "Toxicity Estimation of Unspecific Medicinal Antiviral Agents for Prophylaxis and Therapy of Hazard and Especially Hazard Viral Infections", Antibiotics and Chemotherapy, 2009, vol. 54, Nos. 3-4, pp. 11-14.

Demchenko et al., Synthesis and Anti-Virus activity of [1,3,4]thiadiazolo-[2,3-c][1,2,4]triazine; Journal of Organic and Pharmaceutical Chemistry, 2003, vol. 1, issue 1-2, pp. 55-58.

El-Badawi et al., "Synthesis and biological evaluation of some novel N,N'-bis-(1,2,4-Triazin-4-yl) dicarboxylic acid amides and some fused rings with 1,2,4-triazine ring", Phosphorus, Sulfur and Silicon, 2002, vol. 177, pp. 587-596.

Attaby et al., "Synthesis, reactions, and antiviral activity of 1-(1h-pyrazolo[3,4-b]pyridin-5-yl)ethanone and pyrido [2',3':3,4]pyrazolo[5,1-c][1,2,4]triazine derivatives", Phosphorus, Sulfur, and Silicon, 2006, vol. 181, pp. 1087-1102.

Vynograd et al., "Antiarboviral Properties of different substances of Chemical and Plant Origin", Lviv Scientific-Research Insitute of Epidemiology and Hygiene, Mikrobiologichnii Zhurnal, 2001, vol. 63, No. 2, pp. 14-19.

Rusinov et al., Synthesis and antiviral Activity of 6-nitro-7-oxo-4,7-dihydroazolo-[5,1-c][1,2,4]triazines, Khimiko-farmatsevtichesk Zhurnal, 1990, vol. 24, No. 9, pp. 646-650.

Kushnir et al., "Nitroazines. Part XXII. Alkylation and Prototropic Tautomerism of 6-Nitro-7-oxo-1,2,4-triazolo[1,5-a]pyrimidines", Journal of Organic Chemistry, 1993, vol. 29 (3), pp. 629-638.

International Search Report with regard to PCT/RU2014/000794 dated Jan. 15, 2015.

\* cited by examiner

2-METHYLSULPHANYL-6-NITRO-7-OXO-1, 2, 4-TRIAZOLO [5, 1-C] [1, 2, 4] TRIAZINIDE L-ARGININE DIHYDRATE ACTIVE TOWARD WEST NILE VIRUS

The invention relates to the field of biologically active compounds and relates to 2-methylsulfanyl-6-nitro-7-oxo-1,2,4-triazolo [5,1-c] [1,2,4] triazinid L-arginine dihydrate having antiviral action for the treatment and prevention of viral diseases in humans and animals, mainly of West Nile fever, and can be used in the chemical and pharmaceutical industry, research laboratories, hospitals and veterinary medicine.

The urgency of the problem of anti-viral therapy, especially given the rapid mutation of viruses, identification of new pathogens, dangerous and slow viral infections, causes a constant need for new means that would have high efficiency and stability in case of the virus mutation, prolonged action, low toxicity and lack of side effects during the treatment. In this regard, an important factor is the ability to prepare synthetic pharmaceuticals, as well as to create available technology for their preparation.

Currently, the incidence of West Nile fever (hereinafter—WNV) in the world and, in particular, in the Russian Federation continues to grow.

During 10 months of 2012, in the European Union, the Russian Federation and on the territory of neighboring states, there were reported 923 cases of WNV, including in Greece—161, Hungary—17, Italy—50, Romania—14, Algeria—1, Croatia—5, the Republic of Macedonia—6, Israel—83, Kosovo—4, Montenegro—1, the Russian Federation—447, the Palestinian Authority—2, Serbia—69, Tunisia—63 (See www.edc.europa.eu/en/healthtopics/west_nile_feverAVest-Nile-fever-maps/Pages/2012-table.aspx).

According to the Center for Disease Control and Prevention of the United States, 5674 cases of WNV were reported only for September-October 2012 in the United States in 48 states, including 2969 neuroinvasive cases (that is 51%), 3491 (62.0%) patients were hospitalized, 286 cases of which (5.0%) were fatal (See West Nile virus and other Arboviral diseases—United States, 2012//Morbidity and Mortality Weekly Report.—2013.—62(25); 513-517).

WNV epidemic process has a number of peculiarities both in the epidemiological and clinical aspects: early start and late end of the epidemic season, pronounced seasonality of the disease; differences in the clinical manifestations and disease patterns, which are defined by the number of diseased people, their age, territory where the disease was registered, etc. At the same time in "old" and "new" foci of infection, there is an increase in the proportion of rural residents infected with WNV, significant increase in the proportion of infected people from the age group of 20-29 years (although the age category "60 and older" still remains the dominant group), emergence of new clinical manifestations of infection, namely, the change in the structure of WNV infection places—significant increase in the population group that is infected upon departure to the leisure area in the open area, both on the territory of the Russian Federation and foreign countries (See Information letter of the Chief Sanitary Doctor of the Russian Federation G. G. Onishchenko dated Feb. 22, 2013 No.01/1990-13-32 "Forecast of the epidemiological situation regarding West Nile fever in 2013".).

Expansion of the dissemination area of WNV and increased incidence encourages researchers and developers to search for and manufacture effective non-specific antiviral drugs against this infection. However, attempts to study the efficacy of the individual compounds, both in vitro and in vivo (See Odelola H. A. Antiviral activity of Virazole on replication of viruses isolated in Nigeria. In: Siegenthaler W., Lathy R. editors. Current chemotherapy. Vol.1. Washington: American Society of Microbiology.—1978.—Vol.1.—P.334-335; Jordan L, Briese T., Fisher N. et al. Ribavirin inhibits West Nile virus replication and cytopathic effect in neural cells//J. Infect. Dis.—2000.—Vol.182.—R1214-1217. Shahar A., Lustig S., Akov Y. et al. Different pathogenicity of encephalitic togaviruses in organotypic cultures of spinal cord slices//J. Neurosci. Res.—1990.—Vol.25.—R345-352. Anderson J. F., J. J. Rahal. Efficacy of interferon alpha-2b and ribavirin against West Nile virus in vitro /Emerg. Inf. Dis.—2002.—Vol.8, n.1.—P107-108; Loginova S. Ya., Kovalchuk A. B.,Borisevich S. V. et al.; Antiviral activity of an interferon inducer Amixin in experimental West Nile fever// Voprosy Virusologii.—2004.—No.2.—Pp. 8-11; Loginova S. Ya., Borisevich S. V., Pashchenko Yu. I., Bondarev V. P. Ribavirin prophylaxis and therapy of experimental West Nile fever//Antibiotiki i khimioterapiya.—2009—Vol. 54, Nos.11-12.—Pp. 17-20, Loginova S. Ya., Borisevich S. V., Maksimov V. A., Bondarev V. P. Evaluation of toxicity of non-specific medical antiviral agents for the prevention and treatment of dangerous and especially dangerous viral infections//Antibiotiki i khimioterapiya.—2009.—Vol. 54, Nos.3-4.—Pp.11-14.) did not lead to their use for the treatment of WNV.

Given the above, the search for and development of new effective means for the prevention and treatment of WNV are relevant.

Azoloazines containing a bridging atom of nitrogen in the structure of molecule occupy a significant place among a wide range of synthetic medicinal preparations with antiviral action.

The prior art includes tiadiazoloazines exhibiting activity against hepatitis B virus, Coxsackie virus (See A. M. Demchenko, V. V. Kisly, Z. B. Kvacheva, M. O. Lozinsky. Synthesis and antiviral activity of the derivatives of [1,3,4] thiadiazole [2,3-c] [1,2,4] triazine. Journal of Organic and Pharmaceutical Chemistry, 2003, Vol.1, issue.1-2, pp.55-58; M. A. El-Badawi, A. A. El-Barbary, Y. M. Lokshaa, Mai El-Daly. Synthesis and biological evaluation of some novel FN,N'-bis-(1,2,4-Triazin-4-yl)dicarboxylic acid amides and some fused rings with 1,2,4-triazine ring. Phosph., Sulfur, Silicon and Related Elements, 2002, V. 177, pp.587-596).

Pyrazolo[5,1-c] [1,2,4] triazines exhibit antiviral activity against herpes (G. Bravi, A. Goretti Cheasty, J. A. Corfield, R. M. Grimes. 4-Carboxy pyrazole derivates as antiviral agents. WO 2007039146; F. A. Attaby, A. H.H. Elghandour, M. A. Ali, Y. M. Ibrahem. Synthesis, Reactions, and Antiviral Activity of 1-(1H-Pyrazolo[3,4-b]pyridin-5-yl)ethanone and Pyrido[2',3':3,4]pyrazolo [5,1-c][1,2,4]triazine Derivatives. Phosphorus, Sulfur, and Silicon and Related Elements, 2006, v.181, pp.1087-1102.

Triazolo[5,1-a]-1,2,4-triazines exhibit antiviral activity against influenza and herpes (I.A Vynograd, V. A. Plastunoy, M. M. Kozlovs'kii, L. V. Benzel, G. V. Bilets'ka, I. M. Lozins'kii,; E. G. Rogochii, Sholomei, M. D. Anti-arboviral properties of different substances of chemical and plant origin. L'viv. Mikrobiologichnii Zhurnal. 2001, 63, No.2, 14-19; V. L. Rusinov, Ye. N. Ulomsky, O. N. Chupakhin, M. M. Zubairov, A. B. Kapustin, N. I. Mitin et al. Synthesis and antiviral activity of 6-nitro-7-oxo-4,7-digidroazolo [5,1-c] [1,2,4] triazines. Khimiko-Farmatsevticheskii Zhurnal. 1990, No.9, pp. 41-44).

Analysis of the prior art showed that the analogues of 1,2,4-triazolo [1,5-a] triazine-1,2,4-triazolo [1,5-a] pyrimidines are promising directions to search for new antiviral compounds.

The closest in structure and exhibited antiviral activity to the claimed compound (prototype) is the sodium salt 2-methylthio-6-nitro-7-oxo-[5,1-c]-1,2,4-triazin-7-(4H)-one having the formula

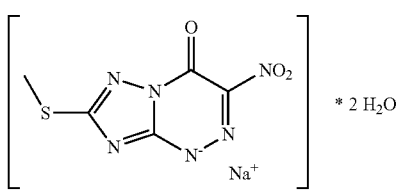

(See patent of the Russian Federation No.2294936 for the invention "Sodium salt 2-methylthio-6-nitro-1,2,4-triazolo[5,1-c]-1,2,4-triazin-7(4H)-one dihydrate having antiviral activity", filing date Jun. 29, 2005, published Mar. 10, 2007).

Technical result to be achieved by the claimed invention is the creation of a new effective means from the range of azoloazines having antiviral activity against a group of RNA viruses, and reduction in the dependence of the active compound on the cell metabolism.

This technical result is achieved due to the creation of a new drug 2-methylsulfanyl-6-nitro-7-oxo-1,2,4-triazolo[5,1-c] [1,2,4]triazinid L-arginine dihydrate having antiviral activity and the following formula

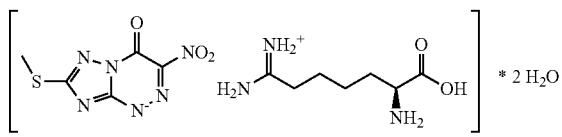

Specified technical result is achieved by the fact that a method for producing 2-methylsulfanyl-6-nitro-7-oxo-1,2,4-triazolo[5,1-c] [1,2,4]triazinid L-arginine dihydrate, which comprises the mixing of arginine dissolved in water and 2-methylthio-6-nitro-7-oxo-1,2,4-triazolo[5,1-c]triazinid sodium dihydrate dissolved in an ethanol-water mixture (1:1), and the resulting mixture is heated on a steam bath, then cooled and the formed precipitate is filtered off and dried.

Technical solutions that match the set of essential features of the claimed invention have been identified, which allows to conclude that the claimed invention corresponds to such patentability criterion as "novelty".

Claimed essential features that predetermine a specified technical result do not obviously follow from the prior art, which allows to conclude that the claimed invention corresponds to such patentability criterion as "inventive step".

Patentability criterion "industrial applicability" is confirmed by the examples of specific applications.

The technical problem is solved by modifying the molecule of the sodium salt 2-methylthio-6-nitro-7-oxo-[5,1-c]-1,2,4-triazin-7-(4H)-one, in particular by replacing the sodium cation by biogenic amino acid arginine fragment.

Synthesis of 2-methylsulfanyl-6-nitro-7-oxo-1,2,4-triazolo[5,1-c] [1,2,4]triazinid-arginine dihydrate is conducted as follows:

2.1 g (0.01 mole) of arginine is charged into a 50 ml round bottom flask equipped with heating bath, stirrer and water-cooled ball reflux condenser, and then 9 ml of water is added. The resulting mixture is adjusted to complete dissolution due to stirring at a room temperature. Further, 2.53 g (0.01 mole) of 2-methylthio-6-nitro-7-oxo-1,2,4 triazolo[5,1-c]triazinid sodium dihydrate is charged into another 50 ml round bottom flask equipped with heating bath, stirrer and water-cooled ball reflux condenser, then 20 ml of ethanol-water mixture is added (1:1). He resulting mixture is heated to 20-25° C. to dissolution.

The resulting solutions are poured together and heated on a steam bath for 10 minutes at a temperature of 90-95° C. The reaction mixture is cooled, and formed precipitate is filtered and then dried at room temperature for one day (24 hours).

The resulting compound 2-methylthio-6-nitro-7-oxo-1,2,4-triazolo [5,1-c] [1,2,4] triazinid L-arginine dihydrate has the following physicochemical characteristics: melting point>300° C.; C—30.30%, H—4.86%, N—32.08%. Chemical formula—$C_{11}H_{18}N_{10}O_5S*2H_2O$. Found: C—30.14%, H—5.06%, N—31.95%. Spectrum $^1$H NMR (400 MHz, $D_2O$), δ (ppm): 1.702 (m, 2H, $CH_2$), 1.918 (m, 2H, $CH_2$), 2.651 (s, 3H, $SCH_3$), 3.245 (m., 2H, $CH_2$), 3.786 (m, 1H, CH).

The claimed compound is a yellow amorphous substance, soluble in water, Dimethylformamide, Dimethyl sulfoxide and insoluble in chloroform, ethanol, and benzene.

Implementation of the claimed invention is confirmed by the examples of embodiment.

EXAMPLE 1

Evaluation of the cytotoxicity of the test compound using a constant cell culture GMK-AH (1D).

To form a continuous monolayer, 1 ml of cell suspension with a density of 200 thousand/ml was added into each tubes and incubate at a temperature (37.0±0.5)° C., 5% $CO_2$.

Then the growth medium was removed and fresh medium containing various concentrations of test drugs (from 1000 to 6.25 g/ml) was added. The tubes were then incubated for 5 days at a temperature (37.0+0.5)° C., 5% $CO_2$.

Using a light microscope, the state of the monolayer cells was observed: partial or complete destruction of the monolayer cells, damage to individual cells, cell syncytium formation. Control samples were tubes with a monolayer, which included maintenance medium without a drug.

Results of the evaluation of cytotoxicity of the test compound indicate that the active substance in a concentration of 500 μg/ml did not cause any visible changes in the cell culture (see Table No.1).

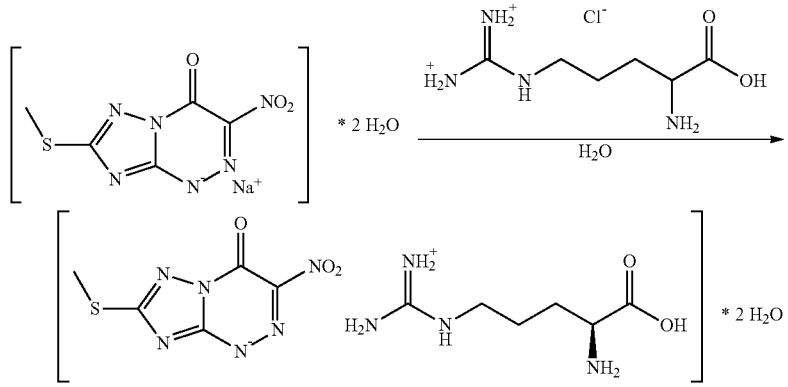

TABLE 1

Study of cytotoxicity of the claimed compound in the cell culture GMK-AH (1D)

| Drug | The frequency of the cytopathic effect of the claimed compound when used in a concentration mg/mL | | | | | | | | TCID50, µg/ml | MIC, µg/ml | ½ MIC µg/ml |
|---|---|---|---|---|---|---|---|---|---|---|---|
| | 1000.0 | 500.0 | 250.0 | 125,0 | 62.5 | 31.3 | 15.5 | 7.8 | | | |
| Claimed compound | 2/4 | 0/4 | 0/4 | 0/4 | 0/4 | 0/4 | 0/4 | 0/4 | 1000.0 | 500.0 | 250.0 |

EXAMPLE 2

Study of the effectiveness of the claimed compound in cell culture GMK-AH (1D) against West Nile virus.

Monolayer of the cell culture GMK-AH (1D) was infected with West Nile virus in a dose of 0.05 PFU/cell. Virus was adsorbed at 37° C., 5% $CO_2$, for 60 minutes. At the end of the incubation, the monolayer was washed three times with maintenance medium containing 100 u/ml penicillin and streptomycin to remove non-adsorbed virus, and test compounds were added at a concentration of ½ MIC. The substance was dissolved in maintenance medium to the desired concentration. For each compound, not less than 10 tubes with a monolayer of cells were used. Incubation was performed at 37° C., 5% $CO_2$ for 48 hours. Next, the cryodestruction of cells was performed and the samples were combined. The infectious titer in the combined samples was determined by titration by forming negative colonies under the agar coating in the cell culture GMK-AH (1D).

Results of the study of the antiviral activity of the claimed compounds indicate that the drug inhibits the reproduction of West Nile virus by 2.31 g, at the same time inhibiting factor is 99.5% (See table No.2).

TABLE 2

Study of the effectiveness of the claimed compound in cell culture GMK-AH (1D) against West Nile virus

| Drug | Concentration of the claimed compound, µg/ml | Level of the virus accumulation of, lg PFU/ml | Reduction of the virus accumulation, lg PFU/ml | Ratio of virus reproduction inhibition, percent |
|---|---|---|---|---|
| Claimed compound | 250.0 | 4.2 | 2.3 | 99.5 |
| K dose | — | 7.8 | — | — |

Thus, the claimed chemical compound is nontoxic in the concentrations used. It has significant antiviral activity in vitro against West Nile virus.

We claim:

1. A compound which is 2-methylsulfanyl-6-nitro-7-oxo-1,2,4-triazolo[5,1-c] [1,2,4]triazinid L-arginine dihydrate, the compound having the formula:

$$\left[ \begin{array}{c} \text{structure} \end{array} \right] * 2\,H_2O.$$

2. A method for the production of 2-methylsulfanyl-6-nitro-7-oxo-1,2,4-triazolo[5,1-c] [1,2,4]triazinid L-arginine dehydrate according to claim 1, which comprises mixing arginine dissolved in water and 2-methylthio-6-nitro-7-oxo-1,2,4-triazolo [5,1-c] triazinid sodium dehydrate dissolved in a water-ethanol mixture (1:1), heating the resulting mixture, and cooling the mixture such that a precipitate is formed; and filtering off and drying the formed precipitate.

3. A method of treating West Nile fever in a patient in need thereof, the method comprising administering an effective amount of the compound of claim 1 to the patient, such that the West Nile fever is treated in the patient.

* * * * *